United States Patent [19] … [11] 4,199,570
Igarashi et al. … [45] Apr. 22, 1980

[54] 1-N-HETERO CONTAINING AMINOGLYCOSIDE DERIVATIVES

[75] Inventors: Kikuo Igarashi, Itami; Junji Irisawa, Nishinomiya, both of Japan

[73] Assignee: Shionogi & Co., Ltd., Osaka, Japan

[21] Appl. No.: 934,595

[22] Filed: Aug. 17, 1978

[30] Foreign Application Priority Data

Sep. 19, 1977 [JP] Japan .................. 52-112840
Sep. 22, 1977 [JP] Japan .................. 52-114176

[51] Int. Cl.$^2$ .................. A61K 31/71; C07H 15/22
[52] U.S. Cl. .................. 424/180; 260/326.2; 260/326.47; 536/10; 536/17 R; 546/221; 546/242
[58] Field of Search .................. 536/10, 17; 424/180

[56] References Cited

U.S. PATENT DOCUMENTS

| | | | |
|---|---|---|---|
| 3,940,382 | 2/1976 | Umezawa et al. | 536/10 |
| 4,051,315 | 9/1977 | Godfrey et al. | 536/10 |
| 4,104,372 | 8/1978 | Umezawa et al. | 536/10 |

Primary Examiner—Johnnie R. Brown
Attorney, Agent, or Firm—Wenderoth, Lind & Ponack

[57] ABSTRACT

Novel aminoglycoside derivatives and their salts containing 2-deoxystreptamine moiety, of which the 1-amino group is acylated by a group represented by the formula:

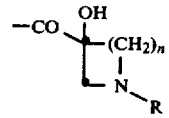

wherein
R is hydrogen, lower alkyl, aralkyl, or aralkoxycarbonyl; and
n is an integer of 1 or 3, effective in treatment and prevention of infectious diseases caused by gram positive and gram negative bacteria.

17 Claims, No Drawings

1-N-HETERO CONTAINING AMINOGLYCOSIDE DERIVATIVES

BACKGROUND OF THE INVENTION

Aminoglycoside antibiotics, for example, streptomycins, kanamycins, gentamicins, tobramycin, etc. have practically been used as broad spectrum antimicrobials effective against gram-positive, gram-negative and acid-fast bacteria. The aminoglycoside antibiotics, however, are sometimes accompanied by undesired side effect such as nephropathy and deafness. Occurrence of resistant strains against the aminoglycosides is another problem to be solved. It has been attempted to modify such aminoglycosides with a specified acyl group at the 1-amino group in order to improve the antimicrobial activity and relatively decrease the side effect. For instance, amikacin, an excellent antimicrobial agent, which is prepared by acylation of the 1-amino group of kanamycin A with 4-amino-2-hydroxybutyric acid, is effective against kanamycin A resistant strains and its toxicity is approximately the same as kanamycin A [described in J. Antibiotic, 25, 695 (1972) by Kawaguchi et al; U.S. Pat. No. 3,781,268 (1973) and J. Antibiotic, 27, 677 (1974)].

The present inventors have found that the antimicrobial spectrum and the potency of activity are improved by acylation of the 1-amino group of aminoglycosides with 3-hydroxypiperidine-3-carboxylic acids or 3-hydroxyazetidine-3-carboxylic acids. The present invention is based upon this finding.

SUMMARY OF THE INVENTION

This invention relates to novel aminoglycoside derivatives having an excellent antimicrobial action. More particularly, this invention relates to novel aminoglycoside antibiotic derivatives and their salts containing a 2-deoxystreptamine moiety of which the 1-amino group is acylated by an azetidinecarboxylic acid or piperidinecarboxylic acid.

The novel aminoglycoside antibiotic derivatives in this invention can be represented by the formula:

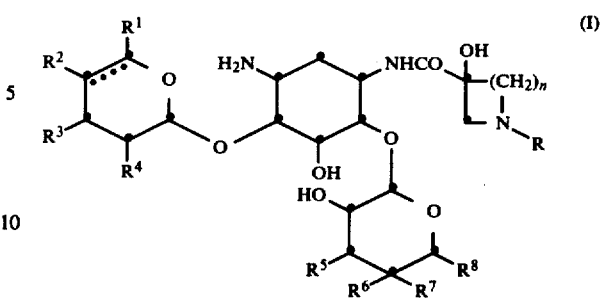

(I)

wherein
R is hydrogen, lower alkyl, aralkyl, or aralkoxycarbonyl;
n is an integer of 1 or 3;
$R^1$ is aminomethyl, hydroxymethyl, 1-aminoethyl, or 1-methylaminoethyl;
$R^2$, $R^3$ and $R^6$ each is hydrogen or hydroxy;
$R^4$ is hydroxy or amino;
$R^5$ is amino or methylamino;
$R^7$ is hydroxy or methyl;
$R^8$ is hydrogen, hydroxymethyl, or carbamoyloxymethyl; and
the dotted line represents the presence or absence of a double bond.

The aminoglycosides used as starting material in this invention containing 2-deoxystreptamine moiety are represented by the general formula (II):

(II)

wherein $R^1$, $R^2$, $R^3$, $R^4$, $R^5$, $R^6$, $R^7$, $R^8$ and the dotted line have the same meaning as mentioned above.

Representative of the compounds (II) and their substituents are shown in Table 1.

Table 1

| Generic Name | $R^1$ | $R^2$ | $R^3$ | $R^4$ | $R^5$ | $R^6$ | $R^7$ | $R^8$ | dotted line |
|---|---|---|---|---|---|---|---|---|---|
| tobramycin | $CH_2NH_2$ | OH | H | $NH_2$ | $NH_2$ | H | OH | $CH_2OH$ | none |
| kanamycin A | " | " | OH | OH | " | " | " | " | " |
| kanamycin B | " | " | " | $NH_2$ | " | " | " | " | " |
| kanamycin C | $CH_2OH$ | " | " | " | " | " | " | " | " |
| deoxykanamycin A | $CH_2NH_2$ | " | H | OH | " | " | " | " | " |
| dideoxykanamycin B (dibekacin) | " | H | " | $NH_2$ | " | " | " | " | " |
| gentamycin $C_1$ | $CH(CH_3)NHCH_3$ | " | " | " | $NHCH_3$ | OH | $CH_3$ | H | " |
| gentamycin $C_2$ | $CH(CH_3)NH_2$ | " | " | " | " | " | " | " | " |
| gentamycin $C_{1a}$ | $CH_2NH_2$ | " | " | " | " | " | " | " | " |
| gentamycin B | " | " | OH | OH | " | " | " | " | " |
| nebramycin factor 4 | " | OH | " | $NH_2$ | $NH_2$ | H | OH | $CH_2OCONH_2$ | " |
| nebramycin factor 5' | " | " | H | " | " | " | " | " | " |
| sisomicin | " | H | " | " | $NHCH_3$ | OH | $CH_3$ | H | double bond |

DETAILED EXPLANATION

In the aforementioned general formula (I), lower alkyl as R means $C_1$ to $C_5$ alkyl, particularly, $C_1$ to $C_3$ alkyl, e.g. methyl, ethyl, propyl, isopropyl, butyl, isobutyl, sec-butyl, t-butyl, pentyl, isopentyl, t-pentyl, neopentyl; aralkyl means $C_7$ to $C_{20}$ aralkyl, e.g. benzyl, phenethyl, phenylpropyl; and aralkoxycarbonyl means $C_8$ to $C_{20}$ aralkoxycarbonyl, e.g. benzyloxycarbonyl, phenoxycarbonyl, 1-phenylethoxycarbonyl, 3-phenylpropoxycarbonyl.

The novel aminoglycoside antibiotic derivatives (I) in this invention include the free bases and salts thereof, particularly non-toxic acid addition salts, for example, salts with inorganic acids such as hydrochloric acid, hydrobromic acid, hydroiodic acid, sulfuric acid, phosphoric acid, carbonic acid, and the like, and salts with organic acids such as acetic acid, fumaric acid, malic acid, tartaric acid, maleic acid, citric acid, mandelic acid, ascorbic acid, gallic acid, and the like.

Representative of the compounds (I) are:
(1) 1-N-(3-hydroxyazetidine-3-carbonyl)tobramycin
(2) 1-N-(3-hydroxyazetidine-3-carbonyl)kanamycin A
(3) 1-N-(3-hydroxyazetidine-3-carbonyl)kanamycin B
(4) 1-N-(1-methyl-3-hydroxyazetidine-3-carbonyl)tobramycin
(5) 1-N-(1-methyl-3-hydroxyazetidine-3-carbonyl)kanamycin A
(6) 1-N-(1-methyl-3-hydroxyazetidine-3-carbonyl)kanamycin B
(7) 1-N-(1-benzyl-3-hydroxyazetidine-3-carbonyl)tobramycin
(8) 1-N-(1-benzyl-3-hydroxyazetidine-3-carbonyl)kanamycin A
(9) 1-N-(1-benzyl-3-hydroxyazetidine-3-carbonyl)kanamycin B
(10) 1-N-(1-benzyloxycarbonyl-3-hydroxyazetidine-3-carbonyl)tobramycin
(11) 1-N-(1-benzyloxycarbonyl-3-hydroxyazetidine-3-carbonyl)kanamycin A
(12) 1-N-(1-benzyloxycarbonyl-3-hydroxyazetidine-3-carbonyl)kanamycin B
(13) 1-N-(3-hydroxypiperidine-3-carbonyl)tobramycin
(14) 1-N-(3-hydroxypiperidine-3-carbonyl)kanamycin A
(15) 1-N-(3-hydroxypiperidine-3-carbonyl)kanamycin B
(16) 1-N-(1-methyl-3-hydroxypiperidine-3-carbonyl)tobramycin
(17) 1-N-(1-methyl-3-hydroxypiperidine-3-carbonyl)kanamycin A
(18) 1-N-(1-methyl-3-hydroxypiperidine-3-carbonyl)kanamycin B
(19) 1-N-(1-benzyl-3-hydroxypiperidine-3-carbonyl)tobramycin
(20) 1-N-(1-benzyl-3-hydroxypiperidine-3-carbonyl)kanamycin A
(21) 1-N-(1-benzyl-3-hydroxypiperidine-3-carbonyl)kanamycin B
(22) 1-N-(1-benzyloxycarbonyl-3-hydroxypiperidine-3-carbonyl)tobramycin
(23) 1-N-(1-benzyloxycarbonyl-3-hydroxypiperidine-3-carbonyl)kanamycin A
(24) 1-N-(1-benzyloxycarbonyl-3-hydroxypiperidine-3-carbonyl)kanamycin B

PREPARATION

Compounds (I) may readily be prepared by acylating the aforementioned aminoglycosides (II) with carboxylic acids represented by the formula:

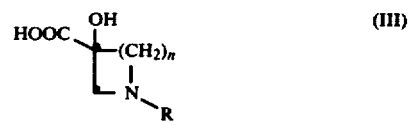

wherein R and n have the same meaning as mentioned above, or the reactive derivatives thereof.

Since the starting aminoglycosides (II) have many functional groups (e.g. amino groups) other than the 1-amino group to be acylated, it is appropriate to optionally protect them by protecting groups before acylation. All of the protecting groups ordinarily used in peptide synthesis, which may readily be removed after acylation of the 1-amino group, may be employed. Such protecting groups include benzyloxycarbonyl which may optionally be substituted on the benzene nucleus, formyl, t-butyloxycarbonyl, t-amyloxycarbonyl, methoxycarbonyl, ethoxycarbonyl, p-toluenesylfonyl, phthaloyl, m-nitrophenylthio, triphenylmethylthio, and the like.

The reactive derivatives of the above mentioned carboxylic acids used as acylating agents include those ordinarily used in peptide synthesis, for example, acid halides, acid azides, acid anhydrides, mixed acid anhydrides, reactive esters and the like. Examples of these derivatives have been described in Synthesis Volume 453 (1972) and Peptide Synthesis Volume 75 to 135 (1966) by M. Bodanszky et al. In the acylating agents, when R is hydrogen atom, it is desirable to protect the skeletal nitrogen atom by a suitable protecting group, for example, the same ones as mentioned in the aminoglycoside protection.

The acylating agents, where n is 1, may be represented by the formula:

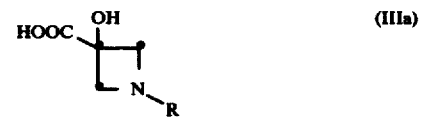

wherein R has the same meaning as mentioned above and may be prepared according to Reaction Scheme 1.

Reaction Scheme 1

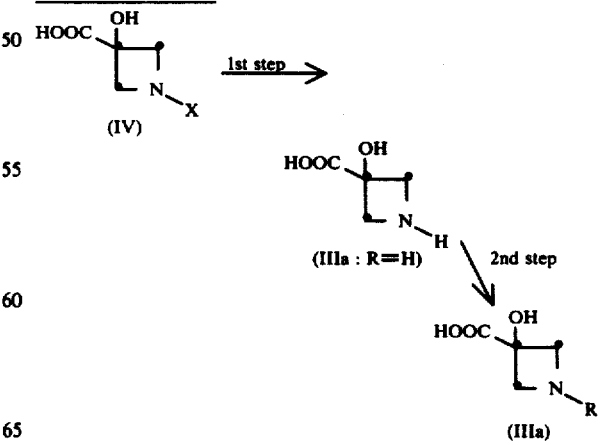

wherein
X is an amino protecting group; and

R has the same meaning as mentioned above.

The starting materials (IV) are known compounds described in Synthesis, 153 (1973).

First Step (Deprotection)

The first step may be carried out by introduction of hydrogen gas into a solution of the starting materials (IV) in a suitable solvent in the presence of a catalyst. The catalysts mean those ordinarily employed in removal of amino protecting groups such as palladium-carbon, Raney Nickel and the like.

Representatives of the solvents used are alcohols (e.g. methanol, ethanol, ethylene glycol), ethers (e.g. diethyl ether, 1,2-diethoxyethane, tetrahydrofuran, dioxane), dimethylformamide, dimethylacetamide, pyridine, water and the like, and they may be used alone or as a mixture of two or more kinds of them.

This reaction proceeds well at room temperature under atmospheric pressure, and if required, may be accelerated by elevation of temperature, increasing pressure, or addition of acid.

Second Step (Alkylation, Aralkylation or Aralkoxycarbonylation)

The second step, alkylation or aralkylation of Compounds (IIIa: R=H) with aldehydes or ketones corresponding to R (alkyl or aralkyl) may be carried out in reductive conditions. The reductive conditions include catalytic hydrogenation with platinum oxide, reduction with reducing agents (e.g. sodium cyanoborohydride), and the like.

The aralkoxycarbonylation of Compounds (IIIa: R=H) is achieved on reaction with carboxylic acids or the reactive derivatives thereof corresponding to R (aralkoxycarbonyl).

The acylating agents, where n is 3, may be represented by the formula:

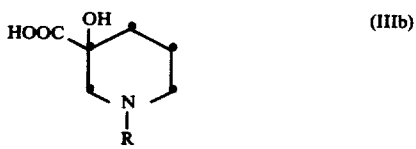

(IIIb)

wherein R has the same meaning as mentioned above, and prepared in a manner as illustrated in Reaction Scheme 2.

Reaction Scheme 2

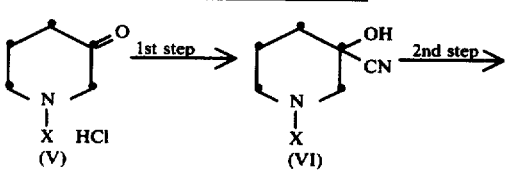

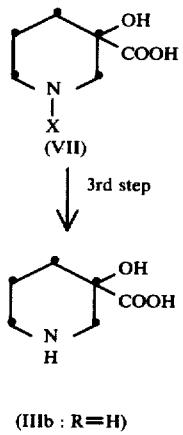

wherein X and R each has the same meaning as mentioned above.

The starting materials (V) are known compounds described in Helv. Chim. Acta., 37, 178 (1954) by B. M. Iselin and K. Hoffmann.

First Step (Cyanation)

The first step, cyanohydrin formation, may be achieved by reaction of Compounds (V) with a cyanating agent. Representative agents are hydrogen cyanide and its derivatives, e.g. sodium cyanide, potassium cyanide, copper cyanide and the like ordinarily employed in cyanation of carbonyl compounds. Preferably, the reaction is accelerated by addition of a basic catalyst when hydrogen cyanide is employed, or by addition of an acidic catalyst when sodium cyanide or potassium cyanide is employed.

An equimolar amount or an excess amount of cyanating agent, preferably about 1.0 to 2.0 moles, is used to one mole of Compounds (V).

This reaction is usually carried out under cooling, at room temperature, or under warming, preferably at 0° to 10° C.

Representatives of solvents employed are alcohols (e.g. methanol, ethanol, ethylene glycol), ethers (diethyl ether, 1,2-dimethoxyethane, tetrahydrofuran, dioxane), dimethylformamide, dimethylacetamide, pyridine, water and the like, and they may be employed alone or as a mixture of two or more kinds of them.

Second Step (Hydrolysis)

This process is carried out by treatment of cyanohydrins (VI) with an acid or base.

The acid means inorganic acids such as hydrochloric acid, sulfuric acid, and the like acids ordinarily employed in hydrolysis, and the base means hydroxides of alkali metals or alkaline earth metals and the like bases ordinarily employed in hydrolysis. The reaction is preferably conducted in an aqueous medium, if required under heating.

Third Step (Deprotection)

This step may be carried out in the same manner as mentioned in the first step of Reaction Scheme 1.

Fourth Step (Alkylation, Aralkylation, or Aralkoxycarbonylation)

This process may be carried out in the same manner as described in the second step of Reaction Scheme 1.

The acylation of aminoglycosides in this invention is achieved by reacting the starting aminoglycosides (II), of which the functional groups other than the 1-amino group have been protected, with the active acylating agents in a suitable solvent. In carrying out the acylation, an equimolar amount or an excess amount of acylating agent, preferably about 1.0 to 2.0 moles, is used to one mole of aminoglycosides. The reaction is conducted at a temperature of 0° C. to 50° C., preferably 20° to 25° C.

Examples of the solvent employed are lower alcohols such as methanol, ethanol and ethylene glycol, ethers such as diethyl ether, 1,2-dimethoxyethane, tetrahydrofuran and dioxane, ketones such as acetone and methyl ethyl ketone, dimethylformamide, dimethylacetamide, pyridine, water, and the like, and they may be used alone or as a mixture of two or more kinds of them.

After the termination of acylation, the protecting groups are removed in conventional manners such as treatment with acids or catalytic hydrogenation to yield the objective compounds (I).

EFFECT

The aminoglycoside antibiotic derivatives and the non-toxic salts thereof prepared in this invention exhibit excellent antimicrobial activities. They are several to several ten times more active than the corresponding unacylated aminoglycosides against some species of gram positive and gram negative bacteria. Minimum Inhibitory Concentration (MIC, μg/ml) of the acylated compounds of this invention and the corresponding well-known unacylated aminoglycosides is indicated in Tables 2 and 3.

Table 2

| Bacteria | MIC (μg/ml) | | | |
|---|---|---|---|---|
| Test Compound | Comp. (1) | TOB | Comp. (2) | KM-A |
| Staphylococcus aureus 80285 | 0.78 | 0.78 | 12.5 | >100 |
| Staphylococcus epidermidis TB-302* | 12.5 | 25 | 6.25 | 12.5 |
| Staphylococcus epidermidis TB-775* | >100 | >100 | 50 | >100 |
| Sarcina lutea PCI 1001 | 3.13 | 12.5 | 12.5 | 12.5 |
| Streptococcus pyogenes ATCC 10389 | 25 | 25 | 50 | 100 |
| Escherichia coli TB-705 | 3.13 | 6.25 | 12.5 | >100 |
| Escherichia coli W-677/JR 66* | 3.13 | 25 | 6.25 | >100 |
| Escherichia coli W-677/JR 762* | 3.13 | 100 | 12.5 | >100 |
| Escherichia coli W-677/JR 214* | 3.13 | 100 | 3.13 | >100 |
| Klebsiella pneumoniae Kl 38 | 0.78 | 1.56 | 1.56 | >100 |
| Enterobacter cloacae CI-38 | 0.78 | 0.78 | 3.13 | >100 |
| Serratia marcescens MA-26 | 6.25 | 50 | 12.5 | >100 |
| Citrobactor freundii Ct-31 | 1.56 | 3.13 | 3.13 | >100 |
| Proteus mirabilis Pm-5 | 1.56 | 12.5 | 6.25 | >100 |
| Proteus vulgaris TB-615* | 6.25 | 50 | 6.25 | 100 |
| Proteus inconstans In-27* | 12.5 | 12.5 | 6.25 | >100 |
| Pseudomonas aeruginosa PP-6* | 3.13 | >100 | 6.25 | >100 |
| Pseudomonas aeruginosa TB-121* | 25 | 100 | 25 | >100 |
| Pseudomonas aeruginosa TB-151* | 3.13 | 100 | 6.25 | >100 |

Note:
Comp. (1) = 1-N-(3-hydroxyazetidine-3-carbonyl) tobramycin
TOB = tobramycin
Comp. (2) = 1-N-(3-hydroxyazetidine-3-carbonyl) kanamycin A
KM-A = kanamycin A
*represents tobramycin resistant strains.

Table 3

| Bacteria | MIC (μ/ml) | |
|---|---|---|
| Test Compund | Comp. (3) | TOB |
| Staphylococcus epidermidis TB-775* | 50.0 | 100.0 |
| Escherichia coli W-677/JR-762* | 3.1 | 25.0 |
| Streptococcus pyogenes C-203 | 3.1 | 6.2 |
| Proteus vulgaris TB-615* | 12.5 | 50.0 |
| Proteus mirabilis TB-617 | 3.1 | 6.2 |
| Pseudomonas aeruginosa PP-6* | 12.5 | 100.0 |
| Pseudomonas aerginosa TB-121* | 12.5 | 25.0 |
| Pseudomonas aeruginosa TB-151* | 12.5 | 25.0 |

Note:
Compound (3) = 1-N-(3-hydroxypiperidine-3-carbonyltobramycin
* represents the tobramycin resistant strains.

As seen from Tables 2 and 3, the compounds (I) of this invention are valuable antimicrobial agents effective against various species of gram positive and negative bacteria, and useful as drugs used for humans and other various kinds of animals. They can be used in prevention or treatment of infectious diseases caused by gram positive bacteria (e.g. Staphylococcus aureus, Staphylococcus epidermidis) and gram negative bacteria (e.g. Escherichia coli, Klebsiella pneumoniae, Proteus mirabilis, Proteus vulgaris, Pseudomonas aeruginosa). The compounds (I) of this invention can also be used as disinfectants for preventing the growth of bacteria alive in perishable, feedstuffs, or hygenical materials.

HOW TO USE

The compounds (I) of this invention can be in a wide variety of oral or parenteral dosage forms solely or in admixture with other co-acting substances. The pharmaceutical compositions may be a mixture of 0.01 to 99% of the compounds (I) with a pharmaceutical carrier or carriers which can be a solid material or liquid material in which the compounds (I) are soluble, dispersible, or suspensible. They can be in a unit dosage form. The solid compositions can be in forms of tablets, powder, dry syrups, troches, granules, capsules, pills, suppositories, or like solid preparation. The liquid compositions can be in forms of injections, ointments, dispersions, inhalant, suspensions, solutions, emulsions, syrups, or elixirs. All of diluents (e.g. starch, sucrose, lactose, calcium carbonate, kaolin); bulking agents (e.g. lactose, sugar, salt, glycine, starch, calcium carbonate, calcium phosphate, kaolin, bentonite, talc, sorbitol); binders (e.g. starch, acacia, gelatin, glucose, sodium arginate, tragacanth, carboxymethylcellulose, sorbitol, polyvinylpyrrolidone); disintegrators (e.g. starch, agar, carbonates, sodium laurylsulfate), lubricant (e.g. stearic acid, talc, paraffin, boric acid, silica, sodium benzoate, polyethylene glycol, cocao oil, magnesium sulfate); emulsifying agents (e.g. lecithin, sorbitan monooleate, acacia); suspending agents (e.g. sorbitol, methylcellulose, glucose, sugar syrup, gelatin, hydroxyethylcellulose, carboxymethylcellulose, aluminum stearate gel, hydrogenated fats); solvents (e.g. water, peanut oil, sesame oil, methyl oleate); preservatives (e.g. methyl or ethyl p-hydroxybenzoate, sorbic acid), edible coloring agents, aromatic substances, solubilizing agents, buffers, stabilizing agents, dispersing agents, wetting agents, antioxidants, and the like can be used in the conventional manners as far as they do not act adversely on the compounds (I).

The compounds (I) of this invention, particularly, their sulfates, are readily soluble in water and conveniently used as solutions for intravenous, intramusclar, or subcutaneous injections according to a conventional method. The compound (I) can be dissolved in an ampoule or oily solvent for injection to give an injectable solution in an ampoule; in order to preserve the injectable preparation for a long period of time, it is appropriate to make a vial preparation containing crystals, powder, microcrystals, or lyophilizate of the compounds (I). The vial preparation may be dissolved or suspended in the said solvents for injection immediately before use. The preparation may contain said preservatives.

Further, the compounds (I) of this invention can be used as suppositories, ointments for topical or opthalmic use, powders for topical use, and like preparations preparable according to the methods well-known to those skilled in the art. The external preparation can contain 0.01 to 99% of the compounds (I) of this invention together with a necessary amount of pharmaceutical carrier given above.

This invention also provides a method for treating or preventing infections caused by bacteria in humans or domestic animals, which comprises administering to the humans or animals the compounds (I) of this invention at a divided or single dose of 0.01 to 5 g/kg a day for injection, 0.01 to 10 g/kg a day for oral administration, or 0.01 to 10 a day for topical application at intervals of 3 to 12 hours.

The method is applicable for treating or preventing some infectious diseases caused by bacteria sensitive to the compounds of this invention, e.g. staphylodermia, anthropozoonosis, cystitis, pyelitis, pneumonia, pneumonitis, bronchitis, empyematic, naspharyngitis, tonsillitis, rhinitis, dermatitis, pustulosis, abscess, wound and soft tissue infections, ear infections, osteomyelitis, septicemia, enteritis, urinary tract infections, and pyelonephritis.

Preferably, the compounds (I) of this invention are given to a patient in forms of pharmaceutical preparation, e.g. powder, dry syrup, tablets, troches, granules, capsules, pills, suppositories, injections, ointments, dispersions, inhalant, suspensions, solutions, emulsions, syrups and elixirs. They may be in a unit dosage form, e.g. tablets, troches, capsules, injections, vials, granules or powder in a separate container of package.

The following examples are provided to further illustrate this invention.

EXAMPLE 1

1-N-(3-hydroxyazetidine-3-carbonyl)tobramycin sulfate

Method A (1) A solution of 252 mg (1.0 mmole) of 1-benzyloxycarbonyl-3-hydroxyazetidine-3-carboxylic acid, 116 mg (1.0 mmole) of N-hydroxysuccinimide and 208 mg (1.0 mmole) of dicyclohexylcarbodiimide in 4 ml of dimethylformamide is stirred at room temperature for 3 hours. 3,2',6',3''-Tetra-N-formyltobramycin (300 mg; 0.502 mmole) is added thereto, and the mixture is stirred at room temperature overnight and at 50° C. overnight. The precipitated dicyclohexylurea is filtered off and washed with dimethylformamide. The combined filtrate and washings are mixed with 70 ml of ethyl acetate, allowed to stand for 30 minutes and filtered. The residue is treated with water to yield 317 mg of water-soluble material and 84 mg of water-insoluble viscous material, and the combined filtrate and washings are concentrated to yield 0.42 g of the residue.

The obtained water-soluble material (317 mg) is dissolved in a mixture of 15 ml of water and 15 ml of methanol, and catalytically hydrogenated in the presence of 150 mg of 10% palladium-charcoal under hydrogen atmosphere after one drop of acetic acid is added. The catalyst is filtered off and washed with a mixture of water and methanol. The combined filtrate and washings are concentrated under reduced pressure to yield 261 mg of 1-N-(3-hydroxyazetidine-3-carbonyl)-3,2',6',3''-tetra-N-formyltobramycin as crude product.

The obtained water-insoluble viscous material and the residue (0.42 g) are dissolved in a mixture of 2 ml of N,N-dimethylformamide, 15 ml of water and 15 ml of methanol, catalytically hydrogenated in the same manner as mentioned above to yield 326 mg of 1-N-(3-hydroxyazetidine-3-carbonyl)-3,2',6',3''-tetra-N-fomyltobramycin as crude product (total yield: 587 mg).

Crude 1-N-(3-hydroxyazetidine-3-carbonyl)-3,2',6'3''-tetra-N-formyltobramycin (587 mg) is dissolved in 35 ml of 10% hydrazine monohydrate, adjusted to pH 6 with acetic acid, refluxed for 6 hours, diluted with 700 ml of water, adsorbed on a column of 137 ml of Amberlite CG-50 ($NH_4^+$), and after washing of the column with 1.76 L of water, eluted with a mixture of 1.76 L of 0.4% ammonium hydroxide and 2 L of 0.8% ammonium hydroxide (one fraction: 15 g). Fraction Nos. 91 to 100 are collected and evaporated under reduced pressure to yield 127 mg of 1-N-(3-hydroxyazetidine-3-carbonyl)tobramycin as powder. This powder is dissolved in 0.9 ml of water, and the solution is treated with active carbon, adjusted to pH 5 with 2 N sulfuric acid, mixed with 20 ml of ethanol, allowed to stand at 0° C. for 2 hours and filtered. The residue is washed with ethanol and dried over phosphorus pentoxide under reduced pressure to yield 120 mg of 1-N-(3-hydroxyazetidine-3-carbonyl)tobramycin $2.5H_2SO_4.2.5H_2O$ in 28% overall yield.

$[\alpha]_D^{22.5} + 78.6 \pm 1.2°$ (c=0.994, $H_2O$).

TLC: Rf=0.30 [Rf=0.55 (tobramycin)].

Silica gel 60 $F_{254}$ plate by Merck/solvent system: isopropanol-ammonium hydroxide (1:1).

Elemental Analysis (for $C_{22}H_{42}N_6O_{11}.2.5H_2SO_4.2.5H_2O$): Calcd(%): C, 30.84; H, 6.12; N, 9.81; S, 9.36. Found(%): C, 30.71; H, 5.95; N, 9.75; S, 9.08.

(2) To a solution of 6.225 g (10.4 mmoles) of 3,2',6',3''-tetra-N-formyltobramycin, 3.137 g (1.2 equivalents) of 1-benzyloxycarbonyloxy-3-hydroxyazetidine-3-carboxylic acid and 1.437 g (1.2 equivalents) of N-hydroxysuccinimide in 97 ml of dimethylformamide is added 3.095 g (1.4 equivalents) of dicyclohexylcarbodiimide at room temperature with stirring, and the mixture is stirred at room temperature overnight. The precipitate, which appears, is removed by filtration and washed with dimethylformamide. The combined filtrate and washings are mixed with 600 ml of ethyl acetate. The precipitate, which appears, is collected, washed with ethyl acetate, and dissolved in a mixture of methanol and water (2:1). The solution is concentrated to yield 8.1 g of 1-N-(1-benzyloxycarbonyl-3-hydroxyazetidine-3-carbonyl)-3,2',6',3''-tetra-N-formyltobramycin as powder in 95.8% yield.

The crude 1-N-(1-benzyloxycarbonyl-3-hydroxyazetidine-3-carbonyl)-3,2',6',3''-tetra-N-formyltobramycin (7.2 g; 8.86 mmoles) is dissolved in a mixture of 360 ml of water and 360 ml of methanol and catalytically hydrogenated in the presence of 3.6 g of 10% palladium-charcoal under hydrogen atmosphere for 2 hours. The catalyst is filtered off, and the filtrate is concentrated under reduced pressure to yield 6.9 g of crude 1-N-(3-hydroxyazetidine-3-carbonyl)-3,2',6',3''-tetra-N-formyltobramycin.

The crude product (6.9 g) is dissolved in 15 ml of water and mixed with 95.8 ml of a solution of concentrated hydrochloric acid in methanol (11 ml→65.5 ml). The resulting solution is stirred for 24 hours at 36° C. in an oil bath. After termination of the reaction, the reaction mixture is neutralized with 220 ml of Amberlite IR-45, and the resin is filtered off and washed with water. The combined filtrate and washings are evaporated under reduced pressure. The residue (5.34 g) is adsorbed on a column of 1.2 L of Amberlite CG-50 ($NH_4^+$) and eluted with 3 L of water and 3 L of 1 N aqueous ammonium hydroxide by gradient method (one fraction: 16 ml). Fraction Nos. 296 to 345 are concentrated to yield 4.06 g of 1-N-(3-hydroxyazetidine-3-carbonyl)tobramycin as crude product. This product is chromatographed on a column of 200 g of silica gel (silica gel 60 by Merck) and eluted with a mixture of isopropanol, ammonium hydroxide and chloroform (2:1:1) and then a mixture of isopropanol and ammonium hydroxide (1:1). The eluate is readsorbed on 2.3 L of Amberlite CG-50 ($NH_4^+$) and eluted with 3 L of water and 3 L of 1 N aqueous ammonium hydroxide (one fraction: 18 ml). Fraction Nos. 319 to 348 are concentrated under reduced pressure to yield 2.420 g of 1-N-(3-hydroxyazetidine-3-carbonyl)tobramycin as pure product.

A solution of 2.347 g of 1-N-(3-hydroxyazetidine-3-carbonyl)tobramycin in 20 ml of water is adjusted to pH 4.6 with 6.6 ml of 10% sulfuric acid and mixed with 250 ml of ethanol to give precipitate (3.10 g), and the latter is collected by filtration, washed with ethanol, dissolved in 10 ml of water and mixed with 200 ml of ethanol. The precipitate is collected by filtration, washed with ethanol, dissolved in water, and concentrated under reduced pressure. The residue is dried over phosphorus pentoxide in vacuo, and then allowed to absorb moisture in a desiccator containing a saturated sodium bromide aqueous solution to yield 2.419 g of 1-N-(3-hydroxyazetidine-3-carbonyl)tobramcyin $2.5H_2SO_4.8H_2O$ in 28.5% overall yield.

$[\alpha]_D^{26.0} + 72.0 \pm 1.1°$ (c=1.034, $H_2O$).

Elemental Analysis (for $C_{22}H_{42}N_6O_{11}.2.5H_2SO_4.8H_2O$): Calcd(%):C, 27.64; H, 6.64; N, 8.79; S, 8.39. Found(%): C, 27.48; H, 6.35; N, 8.51; S, 8.20.

Method B (1) To a solution of 3,2',6',3''-tetra-N-formyltobramycin (20.0 g; 33.4 mmoles), 1-benzyloxycarbonyl-3-hydroxyazetidine-3-carboxylic acid (10.1 g; 40.2 mmoles; 1.20 equivalents) and 1-hydroxybenzotriazole (452 mg; 3.34 mmoles; 0.1 equivalent) in 200 ml of dimethylformamide is dropwise added a solution of 8.30 g (40.2 mmoles; 1.20 equivalents) of dicyclohexylcarbodiimide in 100 ml of tetrahydrofuran in a period of 1 5/6 hours, and the mixture is stirred at room temperature for 3⅔ hours. Dicyclohexylurea (7.40 g), which appears, is filtered off and washed with 60 ml of dimethylformamide and then ethyl acetate. To the combined filtrate and washings is slowly added 2.6 L of ethyl acetate with shaking. After 10 minutes, the precipitated solid is collected by filtration and washed with ethyl acetate. The precipitate is treated with 600 ml of hot methanol to give a crystalline compound. The crystallization is completed by adding 3.0 L of diethyl ether to yield 28.3 g of crude 1-N-(1-benzyloxycarbonyl-3-hydroxyazetidine-3-carbonyl)-3,2',6',3''-tetra-N-formyltobramycin having mp. 230° to 242° C. with decomposition. A part of the above product (500 mg) is recrystallized from 250 ml of methanol to yield 435 mg of 1-N-(1-benzyloxycarbonyl-3-hydroxyazetidine-3-carbonyl)-3,2',6',3''-tetra-N-formyltobramycin having mp. 243° to 247° C. as needles.

Elemental Analysis (for $C_{34}H_{48}N_6O_{17}.3/2H_2O$): Calcd(%): C, 48.62; H, 6.12; N, 10.01. Found(%): C, 48.66; H, 6.19; N, 10.03.

$[\alpha]_D^{23} + 92.3 \pm 1.3°$ (c=1.007, dimethylformamide).

(2) The crude product (27.8 g) obtained in the above (1) is dissolved in 1.0 L of a mixture of methanol and water (1:1) and catalytically hydrogenated in the presence of 14 g of 10% palladium-charcoal under hydrogen atmosphere at atmospheric pressure for 2 hours. The catalyst is filtered off and washed with water. The combined filtrate and washings are evaporated under reduced pressure to yield 24 g of the residue, which is dissolved in water, treated with 1.0 g of active carbon, and then filtered through a pyrex filter. The filtrate is evaporated under reduced pressure to yield 22.8 g of 1-N-(3-hydroxyazetidine-3-carbonyl)-3,2',6',3''-tetra-N-formyltobramycin.

(3) To a solution of 22.8 g of the above product in 63.5 ml of water is added 361 ml (0.71 mole; 4.25 equivalents) of hydrochloric acid solution which is prepared from hydrochloric acid (110 ml) and methanol (545 ml), and the mixture is stirred at an internal temperature of 34.5° to 35° C. After 24 hours, the mixture is adjusted to pH 7.15 with 48.0 ml (0.71 mole) of concentrated ammonium hydroxide below 35° C. The resulting solution is concentrated to about 200 ml at 30° C. under reduced pressure. Water (400 ml) is added thereto, and the solution is adsorbed on a column of 2.0 L of Amberlite CG-50 ($NH_4^+$) and eluted with 5.7 L of water and 1 N ammonium hydroxide (a mixture of 388 ml of concentrated ammonium hydroxide and 5312 ml of water) [one fraction: 20 ml]. Pure 1-N-(3-hydroxyazetidine-3-carbonyl)tobramycin (11.10 g) is obtained from Fractions 430 to 492.

Fractions 418 to 429 and Fractions 493 to 518 are combined and rechromatographed on a column of 600 ml of Amberlite CG-50 ($NH_4^+$) with 2.0 L of water and 2.0 L of 0.5 N ammonium hydroxide (a mixture of 68 ml of concentrated ammonium hydroxide and 1932 ml of water) by gradient method [one fraction: 20 ml]. Pure 1-N-(3-hydroxyazetidine-3-carbonyl)tobramycin (1.15 g) is obtained from Fractions 195 to 229. Fractions 230 to 255 are concentrated under reduced pressure to yield 3.69 g of the residue. A part of the residue (3.44 g) is dissolved in 10 ml of water and mixed with 10 ml of isopropanol. The resulting solution is adsorbed on a column of 150 g of slica gel, eluted with a mixture of isopropanol and concentrated ammonium hydroxide (2:1) until Fraction 32, and then eluted with a mixture of isopropanol and concentrated ammonium hydroxide (1:1).

Fractions 54 to 100 are concentrated to about 50 ml under reduced pressure, treated with 300 mg of active carbon, and filtered. The filtrate is chromatographed on a column of 120 ml of Amberlite CG-50 ($NH_4^+$) and eluted with 1 N ammonium hydroxide (one fraction: 20 ml). The objective product (3.19 g) is obtained from Fractions 11 to 16.

Total yield of pure 1-N-(3-hydroxyazetidine-3-carbonyl) tobramycin is 15.44 g (81.7%).

(4) A solution of the product (15.44 g; 27.3 mmoles) in 180 ml of water is treated with 1.5 g of active carbon and filtered. The residue is washed with 70 ml of water. The combined filtrate and washings are adjusted to pH 6.0 with 111.5 ml of 1 N sulfuric acid under stirring at room temperature and then filtered. The filtrate is lyophilized to yield 21.55 g of lyophilizate, which is allowed to stand in a desiccator containing a saturated solution of sodium bromide until the weight becomes constant to give 23.027 g of 1-N-(3-hydroxyazetidine-3-carbonyl)tobramycin.2.5H$_2$SO$_4$.7H$_2$O in 73.5% overall yield.

Elemental Analysis (for C$_{22}$H$_{42}$N$_6$O$_{11}$.5/2H$_2$SO$_4$.7H$_2$O): Calcd(%): C, 28.17; H, 6.56; N, 8.96; S, 8.55. Found(%): C, 28.02; H, 6.69; N, 8.86; S, 8.38.

$[\alpha]_D^{24}+71.3\pm1.0°$ (c=1.063, H$_2$O).

EXAMPLE 2

Preparation of 1-N-(3-hydroxyacetidine-3-carbonyl) kanamycin A sulfate

Method A

To a solution of 180 mg (0.716 mmole) of 1-benzyloxy-3-hydroxyazetidine-3-carboxylic acid and 82.4 mg (0.716 mmole) of N-hydroxysuccinimide in 2.6 ml of dimethylformamide is added 148 mg of dicyclohexylcarbodiimide, and the mixture is stirred at room temperature for 30 minutes. The precipitated dicyclohexylurea is collected by filtration and washed with 1 ml of dimethylformamide. The combined filtrate and washings contain the corresponding reactive ester.

To a solution of 313 mg (0.54 mmole) of 3,6',3''-tri-N-formylkanamycin A in 3 ml of dimethylformamide is added the above reactive ester solution, and the mixture is stirred at room temperature for 5 hours and mixed with the further same amount of the reactive ester solution. After 1.5 hours, the precipitated dicyclohexylurea is removed by filtration and washed with a small amount of dimethylformamide. The combined filtrate and washings are mixed with 150 ml of ethyl acetate and cooled with ice. Precipitate, which appears, is collected by filtration, washed with ethyl acetate and dissolved in a mixture of methanol and water (2:1). The solution is treated with active carbon and evaporated under reduced pressure to yield 405 mg of 1-N-(1-benzyloxycarbonyl-3-hydroxyazetidine-3-carbonyl)-3,6',3''-tri-N-formylkanamycin A.

This product is dissolved in 7 ml of methanol and catalytically hydrogenated in a suspension of 200 mg of 10% palladium-charcoal in 7 ml of water under hydrogen atmosphere. The catalyst is filtered off and the filtrate is concentrated under reduced pressure to yield 307 mg of 1-N-(3-hydroxyazetidine-3-carbonyl)-3,6',3''-tri-N-formylkanamycin A.

This product is dissolved in 0.64 ml of water, mixed with a solution of concentrated hydrochloric acid in methanol (11.0 ml→65.5 ml), and the resulting mixture is stirred for 23 hours at 35° to 37° C. The reaction mixture is diluted with 5 ml of water and neutralized with 20 ml of Amberlite IR-45. The resin is filtered off and washed with water. The combined filtrate and washings are evaporated under reduced pressure to yield 329 mg of a syrup, which is dissolved in 4 ml of water, adsorbed on a column of 153 ml of Amberlite CG-50 (NH$_4$+), and after washing of the column with 440 ml of water, eluted with 1 L of water and 1 L of 1 N aqueous ammonium hydroxide solution by gradient method (one fraction: 12 ml).

Fraction Nos. 73 to 84 are treated with 100 mg of active carbon, and filtered through a pyrex filter (made by Millipor Ltd.). The filtrate is concentrated under reduced pressure to yield 181 mg of 1-N-(3-hydroxyazetidine-3-carbonyl) kanamycin A.

This product is dissolved in 6 ml of water, adjusted to pH 4.6 with 10.85 ml of 0.0955 N sulfuric acid, and concentrated to about 1 to 2 ml under reduced pressure. The residue is mixed with 50 ml of ethanol and cooled. The precipitate is collected by filtration, washed with ethanol, and dissolved in water. The solution is treated with 100 mg of active carbon and filtered through a pyrex filter (made by Millipor Ltd.). The filtrate is lyophilizated and allowed to stand in order to absorb the moisture until the weight becomes constant, and 246 mg of 1-N-(3-hydroxyazetidine-3-carbonyl)kanamycin A. 2H$_2$SO$_4$.7H$_2$O is obtained in 50% overall yield.

mp. 222 (coloring)~246° to 257° C. (decomposition).

Elemental Analysis (for C$_{22}$H$_{41}$N$_5$O$_{13}$.2H$_2$SO$_4$.7H$_2$O): Calcd(%): C, 29.17; H, 6.56; N, 7.73; S, 7.08. Found(%): C, 29.35; H, 6.43; N, 7.52; S, 7.21.

$[\alpha]_D^{22}+78.9\pm1.1°$ (c=1.037, H$_2$O).

Method B (1) To a solution of 19.0 g (32.39 mmoles) of 3,6',3''-triformylkanamycin A, 10.574 g (42.109 mmoles; 1.3 equivalents) of 1-benzyloxycarbonyl-3-hydroxyazetidine-3-carboxylic acid and 438 mg (3.239 mmoles; 0.1 equivalents) of 1-hydroxybenzotriazole in 380 ml of dimethylformamide is dropwise added a solution of 8.688 g (42.109 mmoles; 1.3 equivalents) of dicyclohexylcarbodiimide in 160 ml of dimethylformamide in a period of 2 1/6 hours, and the mixture is stirred at room temperature for 7 hours. Dicyclohexylurea, which appears, is filtered off and washed with 100 ml of dimethylformamide. The filtrate and washings are concentrated to about 200 ml under reduced pressure and cooled with ice. Dicyclohexylurea, which appears, is filtered off and washed with 100 ml of cold dimethylformamide. The combined filtrate and washings are treated with 3.0 L of ethyl acetate to yield a colorless precipitate, which is collected by filtration, and washed with ethyl acetate to yield 27.4 g of 1-N-(1-benzyloxycarbonyl-3-hydroxyazetidine-3-carbonyl)-3,6',3''-tri-N-formylkanamycin A.

(2) The above product (27.4 g; 32.39 mmoles) is dissolved in 200 ml of a mixture of methanol and water (1:1), and catalytically hydrogenated in the presence of 9.5 g of 10% palladium-charcoal under hydrogen atmosphere to yield 24.2 g of 1-N-(3-hydroxyazetidine-3-carbonyl)-3,6',3''-tri-N-formylkanamycin A.

(3) To a solution of 24.2 g (37.39 mmoles) of the above product in 57 ml of water is added 283.5 ml (557 mmoles; 4.3 equivalents) of hydrochloric acid—methanol as described above, and the mixture is stirred at 35° to 36° C. for 22 hours, and diluted with 50 ml of water. The mixture is adjusted to pH 8 with 47.5 ml (704 mmoles) of concentrated ammonium hydroxide and evaporated under reduced pressure. The residue is dissolved in 100 ml of water and the resulting solution is concentrated to yield 71 mg of the residue, which is dissolved in 190 ml of water, adsorbed on a column of 2.0 L of Amberlite CG-50 (NH$_4$+) and eluted with 5.7 L of water and 5.7 L of 1.5 N ammonium hydroxide by gradient method (one fraction: 20 ml). Fractions 321 to 403 are concentrated under reduced pressure, treated with 5 g of active carbon and filtered, and the filtrate is evaporated under reduced pressure to yield 16.6 g of 1-N-(3-hydroxyazetidine-3-carbonyl)kanamycin A is 87.8% yield.

(4) A solution of the above product (16.6 g; 28.44 mmoles) in 250 ml of water is adjusted to pH 4.6 with 102.5 ml of 1 N sulfuric acid, concentrated to about 60–70 ml under reduced pressure, mixed with 700 ml of ethanol and cooled with ice. Colorless precipitate, which appears, is collected by filtration, washed with ethanol and dissolved in 300 ml of water. The solution is evaporated to dryness under reduced pressure. The residue is dissolved in 200 ml of water, treated with 5 g of active carbon, and filtered through a pyrex filter. The filtrate is concentrated under reduced pressure. The residue is dried over phosphorus pentoxide, pulverized and allowed to absorb moisture in a desiccator (57% humidity) containing a saturated sodium bromide aqueous solution to yield 22.85 g of 1-N-(3-hydroxyazetidine-3-carbonyl)kanamycin A.2H$_2$SO$_4$.7H$_2$O in 77.8% yield.

Elemental Analysis (for C$_{22}$H$_{41}$N$_5$O$_{13}$.2H$_2$SO$_4$.7H$_2$O): Calcd(%): C, 29.17; H, 6.56; N, 7.73; S, 7.08. Found(%): C, 29.27; H, 6.56; N, 7.57; S, 7.02.

$[\alpha]_D^{27} + 79.5° \pm 1.2°$ (c = 1.015, H$_2$O).

EXAMPLE 3

Preparation of 1-N-(3-hydroxyazetidine-3-carbonyl) kanamycin B sulfate

To a solution of 307 mg (0.5 mmole) of 3,2′,6′,3″-tetra-N-formylkanamycin B in a mixture of 1 ml of water and 6 ml of dimethylformamide are added 163.3 mg (0.65 mmole) of 1-benzyloxycarbonyl-3-hydroxyazetidine-3-carboxylic acid and 75 mg (0.65 mmole) of N-hydroxysuciinimide under stirring to give a homogeneous solution. Dicyclohexylcarbodiimide (161 mg; 0.78 mmole) is added thereto, and the reaction mixture is stirred at room temperature for 24 hours. Dicyclohexylurea, which appears, is collected by filtration and washed with 2 ml of dimethylformamide. The combined filtrate and washings are mixed with 80 ml of ethyl acetate and cooled to 0° C. The precipitate is collected by filtration, washed with ethyl acetate, dissolved in 10 ml of water, treated with 200 mg of active carbon and filtered through a pyrex filter (made by Millipor Ltd.). The filtrate is concentrated under reduced pressure to yield 452 mg of 1-N-(1-benzyloxycarbonyl-3-hydroxyazetidine-3-carbonyl)-3,2′,6′,3″-tetra-N-formylkanamycin B.

This product is dissolved in 14 ml of 50% methanol and catalytically hydrogenated in the presence of 200 mg of 10% palladium-charcoal under hydrogen atmosphere. The catalyst is filtered off and the filtrate is concentrated under reduced pressure to yield 331 mg of 1-N-(3-hydroxyazetidine-3-carbonyl)-3,2′,6′,3″-tetra-N-formylkanamycin B.

This product is dissolved in 0.8 ml of water mixed with 5.72 ml of a mixture of concentrated hydrochloric acid (11.0 ml) and methanol (54.5 ml), and stirred in a water bath at 35° to 37° C. for 20 hours. The reaction mixture is diluted with 5 ml of water and neutralized with 20 ml of Amberlite IR-45. The resin is filtered off and washed with water. The combined filtrate and washings are adsorbed on a column of 60 ml of Amberlite CG-50 (NH$_4^+$) and after washing of column with 500 ml of water, eluted with 1 L of water and 1 L of aqueous ammonium hydroxide solution by radient method (one fraction: 12 ml). Fractions Nos. 60 to 69 are collected, treated with 100 mg of active carbon, and filtered through a pyrex filter (made by Millipor Ltd.).

The filtrate is adjusted to pH 4.6 with 13.66 ml of 0.0955 N sulfuric acid and concentrated to about 1 to 2 ml under reduced pressure. The residue is mixed with 50 ml of ethanol and cooled with ice. The precipitate is collected by filtration, washed with ethanol, dissolved in 20 ml of water and evaporated to dryness under reduced pressure. The residue is dissolved in 10 ml of water again, treated with 100 mg of active carbon and filtered through a pyrex filter (made by Millipor Ltd.).

The filtrate is lyophilized to yield the anhydrous product, which is allowed to absorb moisture to yield 252 mg of 1-N-(3-hydroxyazetidine-3-carbonyl)kanamycin B.2.5H$_2$SO$_4$.9H$_2$O in 51% overall yield.

$[\alpha]_D^{23.5} + 75.3° \pm 1.1°$ (c = 1.013, H$_2$O).

Elemental Analysis (for C$_{22}$H$_{42}$N$_6$O$_{12}$.2.5H$_2$SO$_4$.9H$_2$O): Calcd(%): C,26.69; H,6.62; N,8.49; S,8.10. Found(%): C,26.63; H,6.37; N,8.28; S,8.38.

EXAMPLE 4

Preparation of 1-N-(1-methyl-3-hydroxyazetidine-3-carbonyl)tobramycin sulfate

To a solution of 100 mg (0.762 mmole) of 1-methyl-3-hydroxyazetidine-3-carboxylic acid in 2 ml of methanol is added 0.3 ml of concentrated sulfuric acid, and the mixture is refluxed under heating for 2 hours. After cooling, the reaction mixture is diluted with 20 ml of water and neutralized with 25 ml of Amberlite IR-45. The resin is filtered off and washed with water.

The combined filtrate and washing are concentrated under reduced pressure to yield 138 mg of methyl 1-methyl-3-hydroxyazetidine-3-carboxylate as a syrupy material (IR: $\nu_{max}^{film}$ 1718 cm$^{-1}$). This is dissolved in 2 ml of dimethylformamide, mixed with 0.38 ml (10 equivalents) of 100% hydrazine monohydrate, allowed to stand at room temperature overnight, concentrated under reduced pressure, adsorbed on 15 ml of Amberlite CG-50 (NH$_4^+$), and eluted with water (one fraction: 5 ml). Fraction Nos. 11 to 50 are evaporated under reduced pressure to yield 72 mg of the residue, which is treated with a mixture of methanol, acetone and ether to yield 50 mg of 1-methyl-3-hydroxyazetidine-3-carboxylic acid hydrazide. This product is dissolved in a mixture of 1.2 ml of dimethylformamide and 0.3 ml of dimethylsulfoxide and mixed with 0.24 ml of 4.25 N solution of hydrochloric acid in dioxane and 0.102 ml (0.756 mmole) of isoamyl nitrite while cooling on a water bath of which the temperature is kept at −50° C.

The reaction mixture is stirred at −20° C. for 50 minutes, cooled to −60° C. and neutralized with 0.144 ml of triethylamine. A solution of 171 mg (0.287 mmole) of 3,2′,6′,3″-tetra-N-formyltobramycin and 0.04 ml of triethylamine in a mixture of 0.6 ml of dimethylformamide and 0.6 ml of dimethylsulfoxide is added thereto. The mixture is stirred at 0° C. overnight. The precipitate is collected by filtration and washed with dimethylformamide. The combined filtrate and washing are mixed with ethyl acetate. The precipitate is collected by filtration, washed with ethyl acetate, dissolved in water, treated with active carbon, and filtered. The filtrate is concentrated under reduced pressure to yield 213 mg of 1-N-(1-methyl-3-hydroxyazetidine-3-carbonyl)-3,2′,6′,3″-tetra-N-formyltobramycin as crude product.

This product is dissolved in 0.5 ml of water, mixed with 2.85 ml of a mixture of concentrated hydrochloric acid (11 ml) and methanol (54.5 ml), stirred at 35° C. for 24 hours, and neutralized with Amberlite IR-45. The resin is filtered off and the filtrate concentrated under reduced pressure. The residue is adsorbed on a column of 20 ml of Amberlite CG-50 (NH$_4^+$) and eluted with 500 ml of water and 500 ml of 0.4% aqueous ammonium hydroxide solution by gradient method (one fraction: 9 ml). Fraction Nos. 80 to 104 are evaporated under reduced pressure to yield 133 mg of 1-N-(1-methyl-3-hydroxyazetidine-3-carbonyl)tobramycin. This product is dissolved in 3 ml of water, adjusted to pH 4.5 with 10% sulfuric acid and 0.09 N sulfuric acid, and mixed with 40 ml of ethanol. The precipitate is collected by filtration, washed with ethanol, dissolved in water, treated with active carbon, and filtered. The filtrate is lyophilized to yield the anhydrous compound, which is allowed to absorb moisture, until the weight becomes constant, and 1-N-(1-methyl-3-hydroxyazetidine-3-carbonyl)tobramycin 2.5 $H_2SO_4 \cdot 9H_2O$ (176 mg) is obtained in 62% overall yield.

$[\alpha]_D^{25} + 71.1° \pm 1.1°$ (c = 1.038, $H_2O$).

Elemental Analysis (for $C_{23}H_{44}N_6O_{11} \cdot 2.5H_2SO_4 \cdot 9H_2O$): Calcd(%): C,27.96; H,6.84; N,8.51; S,8.11. Found(%): C,28.00; H,6.85; N,8.37; S,8.25.

EXAMPLE 5

Preparation of 1-N-(3-hydroxypiperidine-3-carbonyl)tobramycin sulfate

To a solution of 142 mg (0.602 mmole) of 1-benzyl-3-hydroxypiperidine-3-carboxylic acid in 2 ml of dimethylformamide are added 70 mg (0.602 mmole) of N-hydroxysuccinimide and 125 mg (0.602 mmole) of dicyclohexylcarbodiimide, and the mixture stirred for 2 hours, mixed with 300 mg (0.502 mmole) of 3,2',6',3''-tetra-N-formyltobramycin, and stirred at room temperature overnight. Precipitated dicyclohexylurea is filtered off and washed with dimethylformamide. The combined filtrate and washing are mixed with 70 ml of ethyl acetate and allowed to stand for 30 minutes. The precipitate is collected by filtration, washed with ethyl acetate, dissolved in water, and evaporated under reduced pressure. The residue is dissolved in 1 ml of water and mixed with 5 ml of concentrated hydrochloric acid-methanol (11:54:4). The mixture is stirred at 35° C. for 24 hours, and neutralized with 30 ml of Amberlite IR-45. The resin is filtered off and washed with water. The combined filtrate and washing are evaporated under reduced pressure. The residue (430 mg) is adsorbed on a column of 30 ml of Amberlite CG-50 ($NH_4^+$) and the column is washed with 400 ml of water. Fraction Nos. 45 to 57 (one fraction: 12 ml) eluted with 500 ml of water and 500 ml of 0.4% ammonium hydroxide by gradient method is evaporated under reduced pressure to yield 322 mg of the residue, and the latter chromatographed on a column of 16.5 g of silica gel (silica gel 60 made by Merck Co.) and eluted with isopropanol-ammonium hydroxide-chloroform (5:1:1) (one fraction: 10 ml).

Fraction Nos. 3 to 50 are evaporated under reduced pressure to yield 175 mg of 1-N-(1-benzyl-3-hydroxypiperidine-3-carbonyl)tobramycin.

This product is dissolved in a mixture of 5 ml of water and 5 ml of methanol and catalytically hydrogenated at room temperature in the presence of 180 mg of 10% palladium-charcoal overnight. The catalyst is filtered off and washed with water. The combined filtrate and washing are evaporated under reduced pressure to yield 156 mg of the residue, which is adsorbed on 20 ml of Amberlite CG-50 ($NH_4^+$) and eluted with 500 ml of water and 500 ml of 0.4 N ammonium hydroxide by gradient method (one fraction: 8 ml). Fraction Nos. 54 to 61 are evaporated under reduced pressure to yield 118 mg of 1-N-(3-hydroxypiperidine-3-carbonyl)tobramycin.

This product is dissolved in 4 ml of water, adjusted to pH 4.6 with 0.095 N sulfuric acid, and mixed with ethanol. The precipitate is collected by filtration and washed with ethanol. The obtained powder is dissolved in water, treated with active carbon, and evaporated under reduced pressure to yield the residue, which is allowed to absorb moisture to yield 121 mg of 1-N-(3-hydroxypyrrolidine-3-carbonyl)tobramycin 2.5$H_2SO_4 \cdot 9H_2O$ in 24% yield.

$[\alpha]_D^{22.0} + 66.6° \pm 1.1°$ (c = 1.034, $H_2O$).

Elemental Analysis (for $C_{24}H_{46}N_6O_{11} \cdot 2.5H_2SO_4 \cdot 9H_2O$): Calcd(%): C,28.77; H,6.94; N,8.39; S,8.00. Found(%): C,28.92; H,6.80; N,8.40; S,8.18.

EXAMPLE 6

Preparation of 3-hydroxyazetidine-3-carboxylic acid hydrochloride

To a solution of 2.383 g (8.4 mmoles) of crude 1-benzhydryl-3-hydroxyazetidine-3-carboxylic acid in 64 ml of 50% aqueous dioxane is added 2.1 ml of concentrated hydrochloric acid, and the mixture is catalytically hydrogenated for 32 hours in the presence of 924 mg of 10% palladium-charcoal under hydrogen pressure of 5 kg/cm². The catalyst is filtered off and washed with an aqueous dioxane. The combined filtrate and washings are evaporated under reduced pressure during which the precipitating oily material is removed by washing with ether. The residue is washed with acetone and recrystallized from dimethylformamide-acetone to yield 1.051 g of 3-hydroxyazetidine-3-carboxylic acid hydrochloride as prisms in 82% yield.

mp. 201°–202° C. (decomposition).

Elemental Analysis (for $C_4H_7NO_3 \cdot HCl$): Calcd(%): C,31.28; H,5.25; N,9.12; Cl,23.09. Found(%): C,31.35; H,5.39; N,9.07; Cl,22.90.

EXAMPLE 7

Preparation of 1-methyl-3-hydroxyazetidine-3-carboxylic acid

To a solution of 500 mg (3.26 mmoles) of 3-hydroxyazetidine-3-carboxylic acid hydrochloride in 15 ml of water are added 1.06 ml of 37% formalin and 250 mg of platinum oxide monohydrate, and the mixture is kept at ambient temperature under atmospheric pressure for 46 hours. The catalyst is filtered off and washed with water. The combined filtrate and washings are evaporated under reduced pressure. The residue (0.79 g) is dissolved in 10 ml of water, adsorbed on 30 ml of Amberlite IR-120 B (H+), and eluted with 100 ml of 2 N aqueous ammonium hydroxide solution. The eluate is evaporated under reduced pressure. The residue (431 mg) is crystallized from water-acetone to yield 1-methyl-3-hydroxyazetidine-3-carboxylic acid as prisms.

First crop: 320 mg (74.9% yield), mp. 222°–224° C. (decomposition).

Second crop: 34 mg (8.0% yield), mp. 218°–220° C. (decomposition).

Total yield: 354 mg (82.9% yield).

Elemental Analysis (for $C_5H_9NO_3$): Calcd(%): C,45.79; H,6.92; N,10.68. Found(%): C,45.60; H,7.00; N,10.39.

IR: $\nu_{max}^{Nujol}$ 3345, 1608 cm$^{-1}$.

EXAMPLE 8

Preparation of 1-benzyloxycarbonyl-3-hydroxyazetidine-3-carboxylic acid

To a solution of 2.5 g (16.3 mmoles) of 3-hydroxyazetidine-3-carboxylic acid (prepared in Example 6) dissolved in a solution of 2.04 g of sodium hydroxide in 54 ml of water is added 3.34 g (1.2 equivalents) of benzyloxycarbonyl chloride under stirring at room temperature, and the mixture is stirred overnight and then mixed with 10% aqueous sodium hydroxide solution. The resulting alkali solution is washed with ether, adjusted to pH 1 with 10% hydrochloric acid and extracted with ether. The extract is washed with water, dried over sodium sulfate and evaporated under reduced pressure. The residue is crystallized from n-pentane and then recrystallized from ether-n-pentane to yield 3.137 g of 1-benzyloxycarbonyl-3-hydroxyazetidine-3-carboxylic acid as needles, mp. 134°–136° C., in 76% yield.

The crystals are further recrystallized from ether-hexane to yield pure specimen, mp. 136°–137° C.

Elemental Analysis (for $C_{12}H_{13}NO_5$): Calcd(%): C,57.37; H,5.22; N,5.58. Found(%): C,57.44; H,5.19; N,5.41.

IR: $\nu_{max}^{Nujol}$ 3350, 1720, 1675 cm$^{-1}$.

EXAMPLE 9

Preparation of 1-benzyl-3-hydroxypiperidine-3-carboxylic acid

To a solution of 8.13 g of 1-benzyl-3-piperidone hydrochloride in a mixture of 28.8 ml of tetrahydrofuran-water (1:1) and 2.99 ml (36 mmoles) of concentrated hydrochloric acid is added 4.687 g (72 mmoles) of potassium cyanide while keeping at a temperature below 8° C., and the mixture is stirred for 4 hours, additionally mixed with 1.495 ml (18 mmoles) of concentrated hydrochloric acid and 1.172 g (18 mmoles) of potassium cyanide, stirred for 1 hour and extracted with ether. The extract is washed with water, dried over magnesium sulfate, and evaporated under reduced pressure. The oily residue is dissolved in 14.4 ml of concentrated hydrochloric acid, heated at 80° C. for 1 hour, cooled and then filtered. The residue is washed with acetone. The combined filtrate and washing are evaporated under reduced pressure to yield syrupy residue, and the latter is adjusted to pH 8 with 0.25 N aqueous sodium hydroxide solution, washed thrice with chloroform, and slowly adsorbed on a column of 200 ml of Amberlite IR 120B (H+). The column is washed with 1 L of water, and the eluate with 1.28 L of 5 N aqueous sodium hydroxide solution is evaporated under reduced pressure. The residue is crystallized from acetone to yield 1-benzyl-3-hydroxypiperidine-3-carboxylic acid 1.3 hydrate (mp. 103.5°–104.5° C.) as prisms in 60.2% yield, and the latter is recrystallized from dimethylformamide-water-acetone to yield the pure crystalline product (mp. 104°–105° C.), and the latter is dried over phosphorus pentachloride at 70° C. for 48 hours to yield the corresponding anhydrous material (mp. 212°–214° C.).

Elemental Analysis (for $C_{13}H_{17}NO_3$): Calcd(%): C,66.36; H,7.28; N,5.95. Found(%): C,66.44; H,7.32; N,5.94.

We claim:

1. A compound selected from the group consisting of a novel aminoglycoside derivative represented by the formula:

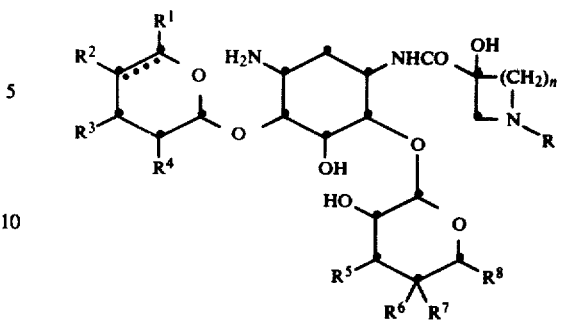

wherein
R is hydrogen, lower alkyl, aralkyl of 7 to 20 carbon atoms, or aralkoxycarbonyl of 8 to 20 carbon atoms;
n is an integer of 1 or 3;
$R^1$ is aminomethyl, hydroxymethyl, 1-aminoethyl, or 1-methylaminoethyl;
$R^2$, $R^3$ and $R^6$ each is hydrogen or hydroxy;
$R^4$ is hydroxy or amino;
$R^5$ is amino or methylamino;
$R^7$ is hydroxy or methyl;
$R^8$ is hydrogen, hydroxymethyl, or carbamoyloxymethyl; and
the dotted line represents the presence or absence of a double bond and a non-toxic acid addition salt thereof.

2. A compound claimed in claim 1 wherein n is an integer of 1.

3. A compound claimed in claim 1 wherein n is an integer of 3.

4. A compound claimed in claim 1 wherein R is hydrogen.

5. A compound claimed in claim 1 wherein $R^8$ is hydrogen or hydroxymethyl.

6. A compound claimed in claim 1 wherein $R^1$ is aminomethyl or hydroxymethyl and $R^8$ is hydrogen or hydroxymethyl.

7. A compound claimed in claim 1 wherein $R^1$ is aminomethyl or hydroxymethyl and $R^8$ is hydroxymethyl.

8. A compound claimed in claim 1 wherein $R^1$ is aminomethyl, $R^2$ is hydroxy, $R^5$ is amino, $R^6$ is hydrogen, $R^7$ is hydroxy, and $R^8$ is hydroxymethyl.

9. A compound claimed in claim 1 namely 1-N-(3-hydroxyazetidine-3-carbonyl)tobramycin.

10. A compound claimed in claim 1 namely 1-N-(1-benzyloxycarbonyl-3-hydroxyazetidine-3-carbonyl)tobramycin.

11. A compound claimed in claim 1 namely 1-N-(3-hydroxyazetidine-3-carbonyl)kanamycin A.

12. A compound claimed in claim 1 namely 1-N-(3-hydroxyazetidine-3-carbonyl)kanamycin B.

13. A compound claimed in claim 1 namely 1-N-(1-methyl-3-hydroxyazetidine-3-carbonyl)tobramycin.

14. A compound claimed in claim 1 namely 1-N-(3-hydroxypiperidine-3-carbonyl)tobramycin.

15. A compound claimed in claim 1 namely 1-N-(1-benzyl-3-hydroxypiperidine-3-carbonyl)tobramycin.

16. A composition which comprises an antibacterially effective amount of a compound according to claim 1 and a pharmaceutically acceptable carrier therefor.

17. A method for the treatment of a bacterial infectious disease in a human or other species of animal which comprises administering to a host suffering from said bacterial infectious disease an antibacterially effective amount of a compound according to claim 1.

* * * * *